(12) United States Patent
Wang

(10) Patent No.: US 12,256,707 B2
(45) Date of Patent: Mar. 25, 2025

(54) SUPERIOR LONG-STAPLE COTTON VARIETY ALLOWING SPINNING 360 N ULTRA-FINE AND HIGH-GRADE COMBED YARNS, AND BREEDING METHOD THEREOF

(71) Applicant: HENAN INSTITUTE OF SCIENCE AND TECHNOLOGY, Xinxiang (CN)

(72) Inventor: Qinglian Wang, Xinxiang (CN)

(73) Assignee: HENAN INSTITUTE OF SCIENCE AND TECHNOLOGY, Xinxiang (CN)

( * ) Notice: Subject to any disclaimer, the term of this patent is extended or adjusted under 35 U.S.C. 154(b) by 73 days.

(21) Appl. No.: 18/218,611

(22) Filed: Jul. 6, 2023

(65) Prior Publication Data
US 2024/0008438 A1  Jan. 11, 2024

(30) Foreign Application Priority Data

Jul. 6, 2022  (CN) .......................... 202210787434.5

(51) Int. Cl.
*A01H 6/60*   (2018.01)
*A01H 5/10*   (2018.01)

(52) U.S. Cl.
CPC .............. *A01H 6/604* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 6,093,876 A * | 7/2000 | Burdett, Jr. ............ | A01H 6/604 435/430 |
| 8,399,748 B2 * | 3/2013 | Spyrou .................. | A01H 6/604 800/278 |
| 11,895,980 B2 * | 2/2024 | Fraser ................ | C12N 15/8286 |
| 2008/0034450 A1 | 2/2008 | Frampton | |

FOREIGN PATENT DOCUMENTS

| CN | 107211887 A | | 9/2017 | |
|---|---|---|---|---|
| CN | 108541578 A | | 9/2018 | |
| CN | 109197571 A | | 1/2019 | |
| CN | 111041126 A | * | 4/2020 | ........... C12Q 1/6895 |

OTHER PUBLICATIONS

GB/T 20392-2006, Test method of properties of cotton fibers by high volume instruments, 2006, pp. 1-5.

* cited by examiner

*Primary Examiner* — Weihua Fan
(74) *Attorney, Agent, or Firm* — Bayramoglu Law Offices LLC

(57) ABSTRACT

A superior long-staple cotton variety allowing spinning 360 N ultra-fine and high-grade combed yarns, and a breeding method thereof are provided. The breeding method includes: conducting distant crossing with *Gossypium barbadense* (*G. barbadense*) L. BMC 1563 as a female parent and Xinluzhong 14 as a male parent; conducting backcrossing with an $F_1$ hybrid as a female parent and BMC1563 as a male parent for three generations; harvesting hybrid seeds of first-generation backcrossing together; harvesting hybrid seeds of second-generation backcrossing separately, and screening; harvesting hybrid seeds of third-generation backcrossing, and screening to obtain an individual $BC_3F_1$; selfing the individual $BC_3F_1$ for 5 generations to obtain BMC18394; and crossing Xinhai 40 as a female parent with the BMC 18394 as a male parent to obtain a first-generation hybrid, and conducting sealing-flower setting for 6 generations to finally obtain a long-staple cotton variety BMC79.

4 Claims, 3 Drawing Sheets

SUPERIOR LONG-STAPLE COTTON VARIETY ALLOWING SPINNING 360 N ULTRA-FINE AND HIGH-GRADE COMBED YARNS, AND BREEDING METHOD THEREOF

CROSS REFERENCE TO THE RELATED APPLICATIONS

This application is based upon and claims priority to Chinese Patent Application No. 202210787434.5, filed on Jul. 6, 2022, the entire contents of which are incorporated herein by reference.

TECHNICAL FIELD

The present disclosure belongs to the technical field of selective breeding of cotton varieties, and in particular relates to a superior long-staple cotton variety allowing spinning 360 N ultra-fine and high-grade combed yarns, and a breeding method thereof.

BACKGROUND

Long-staple cotton is a raw material for spinning high-count yarns and special development industries, and with the improvement of people's living standards and the rapid development of modern spinning technology, demands for long-staple cotton outside China continue to increase. Long-staple cotton is named for its long fibers and is also known as *Gossypium barbadense* (*G. barbadense*) L., and has a genome of AADD. Long-staple cotton originates from South America. Major international production areas of long-staple cotton include Egypt, Sudan, Central Asia, the United States, Morocco, and the like.

Egypt, China, and the United States are major long-staple cotton producers worldwide, whereas output for China is 28.1% of the total long-staple cotton output for the three countries. As special cotton for spinning high-grade yarns, high-quality long-staple cotton has a much higher price than ordinary upland cotton and ordinary long-staple cotton, and has always been in short supply on the international market. Less than 100,000 tons of superior long-staple cotton are produced per year in China, thus 80% or more of the superior long-staple cotton needs to be imported. In addition, most of the long-staple cotton varieties bred in China can only be used to spin 120 N or less yarn due to fiber quality deviations, and have a low acceptance level in textile enterprises, and for 120 N or more high-grade yarns, China mainly relies on imports. Production advantages of China's long-staple cotton have not been fully utilized, and thus China's long-staple cotton has weak market competitiveness and low added values, which seriously plagues the healthy and sustainable development of the cotton industry and the high-end cotton spinning and clothing industry in China. However, there are many problems in long-staple cotton varieties and selective breeding thereof: 1. The general long-staple cotton varieties have poor blight resistance. 2. There is a shortage of long-staple cotton varieties for spinning high-grade yarns. 3. The selective breeding of long-staple cotton varieties is limited by parent sources of a narrow genetic basis, single breeding methods, and insufficient innovation, consequently, making it difficult to breed a superior long-staple cotton variety.

SUMMARY

An objective of the present disclosure is to provide a superior long-staple cotton variety allowing spinning 360 N ultra-fine and high-grade combed yarns, and a breeding method thereof In order to achieve the above objective, the present disclosure adopts the following technical solutions:

A breeding method of a superior long-staple cotton variety allowing spinning 360 N ultra-fine and high-grade combed yarns is provided, including the following steps:

(1) conducting distant crossing with high-quality and high-verticillium wilt-resistance *G. barbadense* BMC1563 as a female parent and a high-yield and high-blight-resistance upland cotton variety Xinluzhong 14 as a male parent; conducting modified backcrossing with an $F_1$ hybrid as a female parent and BMC1563 as a male parent for three generations; harvesting hybrid seeds of first-generation modified backcrossing together; harvesting hybrid seeds of second-generation modified backcrossing separately, and conducting fiber detection and screening; harvesting hybrid seeds of third-generation modified backcrossing, and conducting fiber detection and target trait screening to obtain an individual $BC_3F_1$; and selfing the individual $BC_3F_1$ for 5 generations to obtain BMC18394; and (2) crossing *G. barbadense* L. Xinhai 40 as a female parent with the BMC18394 as a male parent, harvesting hybrid seeds of the crossing separately, and conducting fiber detection and screening to obtain a first-generation hybrid; and conducting sealing-flower selfing for 6 generations to obtain an F7 population, and isolating the F7 population, where from first-generation selling to sixth-generation selfing, fiber detection and identification and screening of mixed onset of blight and verticillium wilt in Xinjiang cotton areas are synchronously conducted, genetically-stable excellent lines with high fiber quality and blight and verticillium wilt resistance are screened out from an isolated population and subjected to a multi-repeat test to determine a fiber quality, and screened lines are subjected to a multi-repeat test, a line-comparison test, and a quality test to finally obtain a long-staple cotton variety BMC79 with high blight and verticillium wilt resistance and long, fine, and strong fibers that allows spinning 360 N combed yarns.

Further, the high-verticillium wilt-resistance *G. barbadense* L. BMC1563 is an individual bred as follows: treating *G. barbadense* Xinhai 21 for 154 h under a negative vacuum pressure of −0.32 sowing treated *G. barbadense* Xinhai 21 in a field, and subjecting M1 and M2 populations to sealing-flower selling.

Further, the high-yield and high-blight-resistance upland cotton variety Xinluzhong 14 is bred as follows: sowing upland cotton Xinluzhong 14 in an artificial blight and verticillium wilt mixed severe disease nursery, and screening out a disease-resistant individual; and cultivating a stem apex of the disease-resistant individual on a *Fusarium oxysporum* (*F. oxysporum*)-containing modified. MS medium in a greenhouse, and after seedling establishment, transplanting a seedling in a field.

A long-staple cotton variety BMC79 is provided, where the long-staple cotton variety has a seed cotton yield per unit of 362.00 kg/mu, and a fiber of the long-staple cotton variety has an average upper-half length of 38.88 mm, a uniformity index of 90.35%, a specific strength at break of 58.50 cN/tex, a micronaire value of 3.23, and a diameter of 9.97 μm.

The present disclosure has the following advantages: In the present disclosure, through technologies such as distant crossing, backcrossing breeding, identification and screening of disease resistance, and weighted balancing selection of fiber quality, many years of southern breeding+northern breeding, and introgression of blight and verticillium wilt-resistance and high-fiber-quality genes of *G. barbadense* L. and upland cotton, high-yield and high-blight-resistance genes of the upland cotton Xinluzhong 14 are successfully transferred into the high-quality and high-verticillium wilt resistance *G. barbadense* L. BMC1563 to obtain a *G. barbadense* L. variety BMC79 with high blight and verticillium wilt resistance and long, fine, and strong fibers. The *G. barbadense* L. variety BMC79 has a seed cotton yield per unit of 362.00 kg/mu (ginned cotton yield per unit: 106.97 kg/mu), and a fiber of the *G. barbadense* L. variety BMC79 has an average upper-half length of 38.88 mm, a uniformity index of 90.35%, a specific strength at break of 58.50 cN/tex, a micronaire value of 3.23, and a diameter of 9.97. A fiber of the cotton variety Giza 45 has a length of 34.60, a uniformity index of 85.60%, a specific strength at break of 42.80 cN/tex, a micronaire value of 3.24, and a diameter of 10.20. The major indexes such as fiber length, strength, uniformity, micronaire value, and fiber diameter of the BMC79 have fully reached or exceeded these indexes of the Egyptian Giza 45. According to trial spinning results, fibers of the BMC79 can be used to spin 360 N combed yarns. The BMC79 can be demonstrated and cultivated in long-staple cotton areas to improve the market competitiveness of high-quality high-grade long-staple cotton and textile and clothing.

DETAILED DESCRIPTION OF THE EMBODIMENTS

Example

Figure 1:
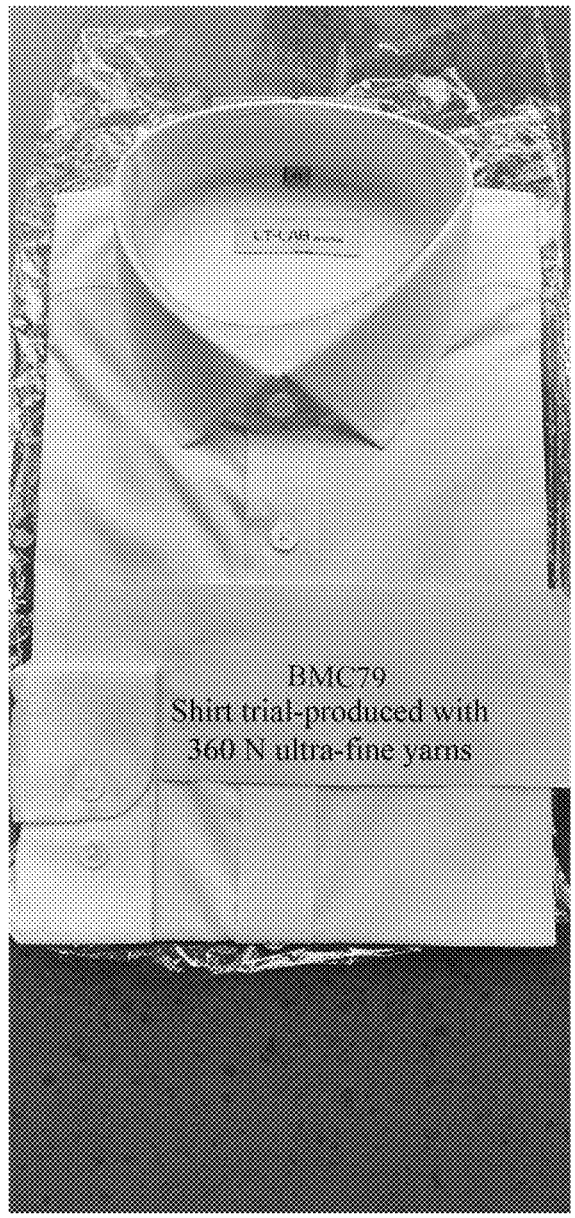
FIG. 1 shows a shirt trial-produced with yarns spun from the 360 N variety of the present disclosure.
Figure 2:
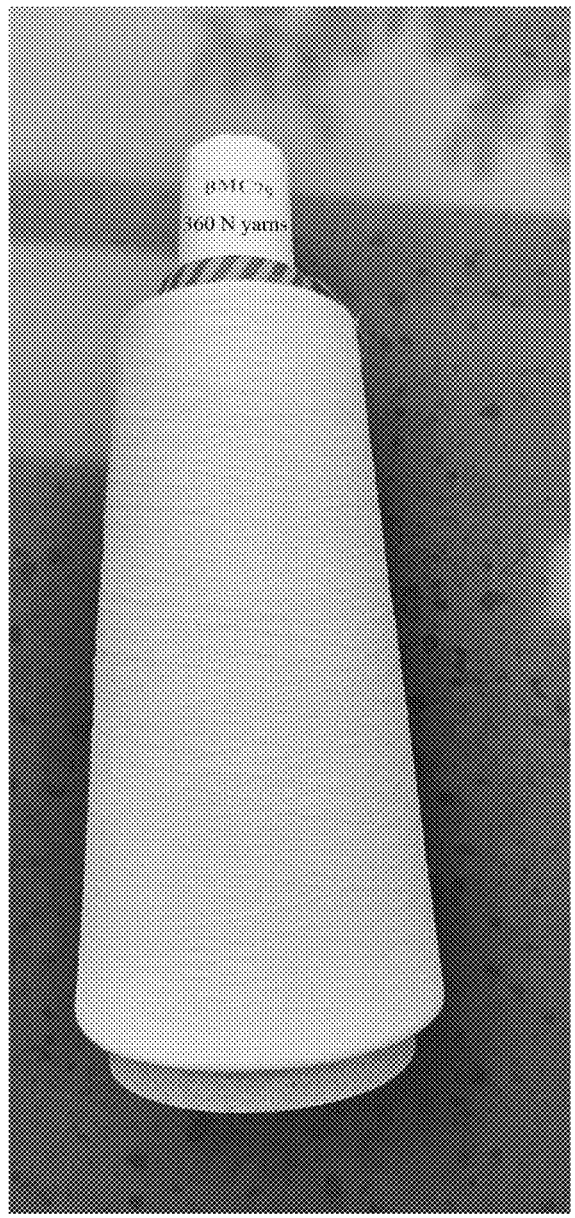
FIG. 2 shows yarns spun from the 360 N variety of the present disclosure.
Figure 3:
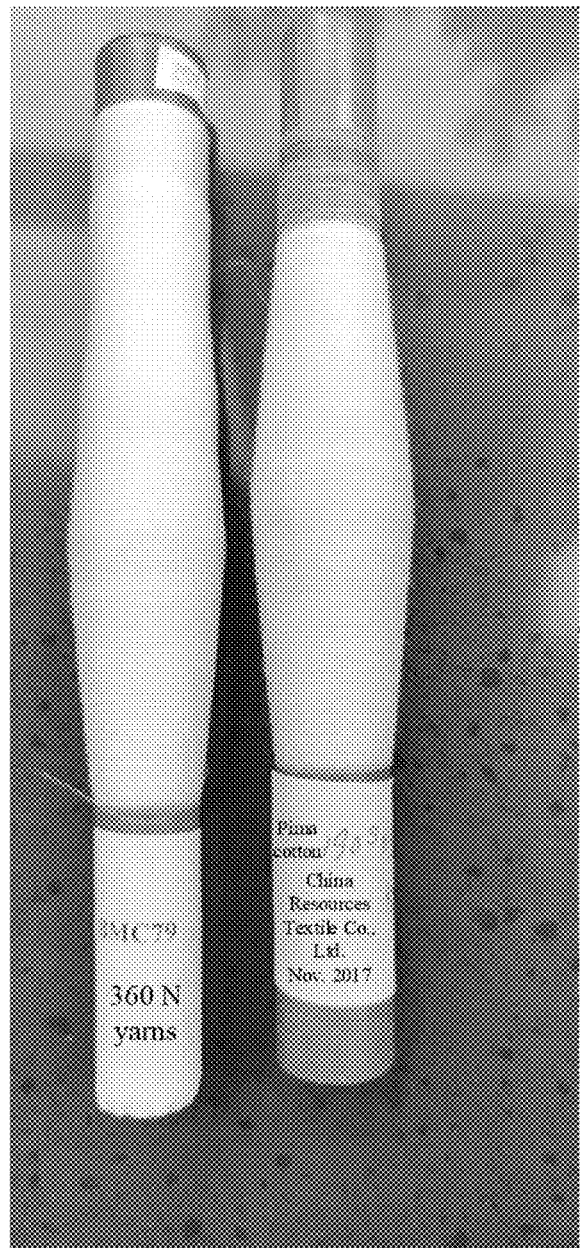
FIG. 3 is a comparison diagram of FIG. 2 of the present disclosure and yarns spun from Pima cotton.

A breeding method of a superior long-staple cotton variety allowing spinning 360 N ultra-fine and high-grade combed yarns was provided, including the following steps: *G. barbadense* Xinhai 21 was treated for 154 h under a negative vacuum pressure of −0.32 MPa and then sown in a field, M1 and M2 populations were subjected to sealing-flower selfing, and a high-quality and high-verticillium wilt-resistance individual BMC1563 was screened out; upland. cotton Xinluzhong 14 was sown in an artificial blight and verticillium wilt mixed severe disease nursery, a disease-resistant individual was screened out, a stem apex of the disease-resistant individual was cultivated on a *F. oxysporum*-containing modified MS medium in a greenhouse, and after seedling establishment, a seedling was transplanted in a field, and a high-blight and verticillium wilt-resistance individual Xinluzhong 14 was screened out; the BMC1563 as a female parent was crossed with the high-blight and verticillium wilt-resistance individual Xinluzhong 14 as a male parent to obtain an $F_1$ hybrid, and the $F_1$ hybrid as a female parent was backcrossed with the BMC1563 as a male parent for three generations to obtain $BC_3F_1$; the $BC_3F_1$ was selfed for 4 generations to obtain BMC18394; and Xinhai 40 as a female parent was crossed with the BMC18394 as a male parent to obtain a first-generation hybrid, and the first-generation hybrid was subjected to sealing-flower selfing for 6 generations to finally obtain a long-staple cotton variety BMC79. During the selective breeding, $F_2$, $F_4$, and $F_6$-generation populations were subjected to weighted balancing selection of fiber quality, that is, an individual or line BMC79 with a fiber length and a fiber strength greater than an average fiber length and an average fiber strength of a population and with a fiber micronaire value and a fiber diameter smaller than an average fiber micronaire value and an average fiber diameter of the population was screened out. The variety had a seed cotton yield per unit of 362.00 kg/mu, and a fiber of the long-staple cotton variety had an average upper-half length of 38.88 mm, a uniformity index of 90.35%, a specific strength at break of 58.50 cN/tex, a micronaire value of 3.23, and a diameter of 9.97 μm.

Application Example

In the winter of 2003, in Sanya of Hainan, a high-quality and high-verticillium wilt-resistance long-staple cotton variety BMC1563 as a female parent was crossed with an upland cotton variety Xinluzhong 14 as a male parent.

In 2004, in Korla of Xinjiang, $F_1$ (BMC1563X Xinluzhong 14) as a female parent was backcrossed with BMC1563 as a male parent, and seeds of the backcrossing were harvested together.

In the winter of 2004, in Sanya of Hainan, $BC_1F_1$ (BMC1563X Xinluzhong 14) as a female parent was backcrossed with BMC1563 as a male parent, and seeds of the backcrossing were collected separately and subjected to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2005, in Korla of Xinjiang, $BC_2F_1$ (BMC1563X Xinluzhong 14) as a female parent was backcrossed with BMC1563 as a male parent, and seeds of the backcrossing were harvested. separately and subjected to fiber detection; and individuals were compared in terms of traits such as plant type, fiber quality, single-plant boll formation, single-boll weight, lint percentage, and fruit-bearing shoot nodes to obtain a $BMC3F_1$ seed (BMC1563X Xinluzhong 14) with excellent comprehensive traits.

In the winter of 2005, in Sanya of Hainan, the BMC3F 1 (BMC1563X Xinluzhong 14) seed was sown and subjected to sealing-flower selfing; and seeds of the selfing were collected separately and subjected to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2006, in Korla of Xinjiang, the BMC3$F_2$ (BMC1563X Xinluzhong 14) seed was sown, non-disease-resistant individuals were eliminated, and disease-resistant individuals were subjected to sealing-flower selfing; seeds of the selfing were collected separately and subjected. to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2007, in Korla of Xinjiang, the BMC3$F_3$ (BMC1563X Xinluzhong, 14) seed was sown, non-disease-resistant individuals were eliminated, and disease-resistant individuals were subjected to sealing-flower selfing; seeds of the selfing were collected separately and subjected to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2008, in Aksu of Xinjiang, the BMC3$F_4$ (BMC1563X Xinluzhong, 14) seed was sown, non-disease-resistant individuals were eliminated, and disease-resistant individuals were subjected to sealing-flower selling; seeds of the selling were collected separately and subjected to fiber detection; and individuals with an upper-half fiber length of less than or equal to 37.00 mm, a specific strength at break of less than or equal to 50,00 cN/tex, a micronaire value of less than 3.00, or a micronaire value of more than 3.60 were eliminated.

In 2009, in Aksu of Xinjiang, the BMC3$F_5$, (BMC1563X Xinluzhong 14) seed was sown, non-disease-resistant individuals were eliminated, and disease-resistant individuals were subjected to sealing-flower selfing; seeds of the selfing were collected separately and subjected. to fiber detection; and individuals with an upper-half fiber length of less than or equal to 37,00 mm, a specific strength at break of less than or equal to 50.00 cN/tex, a micronaire value of less than 3.00, or a micronaire value of more than 3.60 were eliminated, and an individual with blight and verticillium wilt resistance and high fiber quality was screened out and named BMC18394.

In 2010, in Aksu of Xinjiang, a long-staple cotton variety Xinhai 40 with high quality and verticillium wilt resistance as a female parent was crossed with the long-staple cotton variety BMC18394 with blight and verticillium wilt resistance and high fiber quality as a male parent.

In the winter of 2010, in Sanya of Hainan, $F_1$ (Xinhai 40XBMC18394) was sown and subjected to sealing-flower selfing; and seeds of the selfing were collected together.

In 2011, in Aksu, Aral, Korla, or the like of Xinjiang, $F_2$ (Xinhai 40XBMC18394) was sown and subjected to sealing-flower selfing, low-generation large populations were subjected to multi-ecological selection, and seeds were harvested separately and subjected to fiber detection and weighted balancing selection of fiber quality; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In the winter of 2011, in Sanya of Hainan, $F_3$ (Xinhai 40XBMC18394) was sown and subjected to sealing-flower selfing; seeds of the selfing were collected separately and subjected to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2012, in Aksu, Aral, Korla, or the like of Xinjiang, $F_4$ (Xinhai 40XBMC18394) was sown and subjected to sealing-flower selfing, low-generation large populations were subjected to multi-ecological selection and weighted balancing selection of fiber quality, and seeds were harvested separately and subjected to fiber detection; and individuals with an upper-half fiber length of less than or equal to 37.00 mm, a specific strength at break of less than or equal to 50.00 cN/tex, a micronaire value of less than 3.00, or a micronaire value of more than 3.60 were eliminated.

In 2013, in Aksu of Xinjiang, $F_5$ (Xinhai 40XBMC18394) was sown in a blight and verticillium wilt mixed disease nursery; disease-resistant lines were screened out, and non-disease-resistant lines were eliminated; 20 individuals were randomly selected from each disease-resistant line and subjected to fiber detection; and lines with an upper-half fiber length of less than or equal to 37.00 mm, a specific strength at break of less than or equal to 50.00 cN/tex, a micronaire value of less than 3.00, or a micronaire value of more than 3.60 were eliminated.

In 2014, in Aksu of Xinjiang, $F_6$ (Xinhai 40XBMC18394) was sown in a blight and verticillium wilt mixed disease nursery; disease-resistant lines were screened out, and non-disease-resistant lines were eliminated; 20 individuals were randomly selected from each disease-resistant line and subjected to fiber detection; and lines with an upper-half fiber length of less than or equal to 37.00 mm, a specific strength at break of less than or equal to 50.00 cN/tex, a micronaire value of less than 3.10, or a micronaire value of more than 3.60 were eliminated to obtain an excellent line.

In 2015, in Aksu of Xinjiang, $F_7$ (Xinhai 40XBMC18394) was sown, excellent lines were subjected to multi-repeat and line-comparison tests; non-disease-resistant lines were eliminated, and a disease-resistant line was subjected to sealing-flower selfing; and 20 individuals were randomly selected from each line and subjected to fiber detection.

In 2016, in Aksu of Xinjiang, selected lines were sown and subjected to multi-repeat and line-comparison tests. The lines were compared in terms of traits such as plant type, fiber quality, single-plant boll formation, lint percentage, single-boll weight, and disease resistance to obtain a genetically-stable line with prominent comprehensive traits of Xinhai 40 X [(high-quality and high-verticillium wilt-resistance variety BMC 1563 X high-blight and verticillium wilt-resistance variety Xinluzhong 14) BMC18394], which was named BMC79. A fiber quality of the BMC79 was detected by the Cotton Quality Supervision, Inspection, and Test Center of the Ministry of Agriculture according to the GB/T 20392-2006 *"Test Method of Properties of Cotton Fibers by High Volume Instruments"*, and results were as follows (Table 1): the fiber had an average upper-half length of 38.88 mm, a uniformity index of 90.35%, a specific strength at break of 58.50 cN/tex, a micronaire value of 3.23, and a diameter of 9.97 μm. According to trial spinning results of China Resources Textile Co., Ltd., the fiber could be used to spin 300 N to 360 N extra-high-count yarns, and a strength of COMNE300 produced by the fiber was 14.5% higher than a strength of the optimal Egyptian long-staple cotton Giza 45 (G45) worldwide.

TABLE 1

Test results of cotton fibers by the Cotton Quality Supervision,
Inspection, and Test Center of the Ministry of Agriculture of China
Test time: January 2018

| Variety name | Sampling site | Average upper-half length/mm | Uniformity index/% | Specific strength at break/cN · tex$^{-1}$ | Micronaire value | Diameter/μm | Spinning uniformity index |
|---|---|---|---|---|---|---|---|
| BMC79 | Korla Aral | 38.88 | 90.35 | 58.50 | 3.23 | 9.97 | 251.17 |
| Giza 45 | Korla Aral | 34.60 | 85.60 | 42.80 | 3.24 | 10.20 | 184.00 |

Notes:
1. Testing basis: GB/T20392-2006 *"Test Method of Properties of Cotton Fibers by High Volume Instruments"*.
2. Main instrument: large-capacity fiber detector (ZXYQ 09-1).

TABLE 2

The genetic resource BMC18394 has the following depository
information at the China Center for Type Culture Collection
(CCTCC) Depository.

| Genetic resource | Despot information |
|---|---|
| BMC18394 | CCTCC Accession No .: P202406 |
| | Date of deposit: Mar. 6, 2024 |
| | Culture name: G. barbadense L. seed BMC18394; |
| | Gossypium barbadense Linn. |
| | Depository: China Center for Type Culture |
| | Collection (CCTCC) Wuhan University, No. 299 |
| | Bayi Road, Wuchang District, Wuhan City, Hubei |
| | Province, China. |

TABLE 3

The genetic resource BMC18394, CCTCC Accession No.: P202406,
has the following morphological and physiological traits:

| | |
|---|---|
| Species: | *Gossypium barbadense* L.: G. barbadense L. seed BMC18394; Gossypium barbadense Linn. (CCTCC Accession No.: P202406) |
| Areas of Adaptation | Xinjiang, China and similar areas of the world suitable for island cotton cultivation. |
| Applicant | Hualan Road, Xinxiang, Henan, China Henan Institute Science and Technology |
| General | |
| Plant Habit | Intermediate. Plant type tube type, Compact, Thick stalks. |
| Foliage | Dense. Cotyledon: kidney shaped. Stems erect. |
| Stem Lodging | |
| Fruiting Branch | No branches |
| Growth | Intermediate |
| Leaf Color | Dark Green |
| Boll Shape | Length more than width. Boll ovoid, sharp. |
| Boll Breadth | Broadest at base |
| Maturity | |
| Date of 50% open bolls | 140 days |
| Plant | |
| 1st Fruiting Branch (cm from cotyledonary node) | 7.3 |
| No. of Nodes to 1st Fruiting Branch (excluding cotyledonary node) | 2.5 |
| Mature Plant Height in cm (from cotyledonary node to terminal) | 95.0 cm |

TABLE 3-continued

The genetic resource BMC18394, CCTCC Accession No.: P202406,
has the following morphological and physiological traits:

| | |
|---|---|
| Leaf (Upper most, fully expanded leaf) | |
| Type | NORMAL Leaves 5-lobed, Leaves larger, deep crack, The leaves are dark green. |
| Pubescence | Medium. (The leaf blade has fluff) |
| Nectaries | Present |
| Glands | |
| Leaf | Present |
| Stem | Present |
| Calyx Lobe | Present |
| Flower | |
| Petals | Yellow |
| Pollen | Golden yellow |
| Petal Spot | Present. The petals have erythema at the base. |
| Seed | 12.2 g |
| Seed Index (g/100, fuzzy basis) | |
| Boll | |
| Lint percent (%) Picked | 32.5%~34.0% |
| Number of Seeds per Boll | 20.3 |
| Boll weight | 3.4 g |
| Number of Locules per Boll | 3 To 4 (Many with 3) |
| Boll Type | OPEN (Bell ovoid) |
| Fiber Properties | |
| Specify Method (HVI or other) | HVICC standard (HVICC) |
| Length (mm/in, 2.5 SL) | 1.48 in/37.5 mm |
| Uniformity (%) | 89.6 |
| Strength Tl (cN/tex) | 52.3 cN/tex |
| Elongation E1 (%) | 6.9% |
| Micronaire (x) | 3.5 |
| Diseases and Pests | |
| Fusarium Wilt | High resistance to fusarium wilt, the disease index was 3.7. |
| Verticillium Wilt | High resistance to verticillium wilt. The disease index was 5.5. |
| Bacterial Blight | Good resistance |
| Root-Knot Nematode | Unknown |
| Boll Weevil | Unknown |
| Bollworm | Moderately resistant |
| Reniform Nematode | Unknown |
| Lygus | Moderately resistant |
| Pink Bollworm | Resistant |
| Tobacco Bud Worm | Resistant |

What is claimed is:

1. A *Gossypium barbadense* L. cotton plant seed having accession number of China Center for Type Culture Collection (CCTCC) No. P202406, wherein the cotton plant seed is collected from a *G. barbadense* L. cotton plant having an upper-half fiber length greater than 37.00 mm, a break strength of greater than 50.00 cN/tex, and a micronaire value of between 3.00 and 3.60.

2. A *Gossypium barbadense* L. cotton plant seed having accession number of China Center for Type Culture Collection (CCTCC) No. P202406, wherein a cotton plant grown from the seed has an upper-half fiber length greater than 37.00 mm, a break strength of greater than 50.00 cN/tex, and a micronaire value of between 3.00 and 3.60.

3. A *Gossypium barbadense* L. cotton plant grown from a *G. barbadense* L. cotton plant seed having accession number of China Center for Type Culture Collection (CCTCC) No. P202406, wherein the *G. barbadense* L. cotton plant has an upper-half fiber length greater than 37.00 mm, a break strength of greater than 50.00 cN/tex, and a micronaire value of between 3.00 and 3.60.

4. A method of producing a long-staple and *verticillium* wilt resistant hybrid *Gossypium barbadense* L. cotton plant seed, comprising:
    crossing a long-staple variety *Gossypium barbadense* L. cotton plant as a female parent with a *G. barbadense* L. cotton plant according to claim 3 as male parent,
    collecting hybrid *G. barbadense* L. cotton plant seeds from the female parent.

* * * * *